(12) United States Patent
Staats et al.

(10) Patent No.: US 9,026,392 B2
(45) Date of Patent: May 5, 2015

(54) METHOD AND APPARATUS FOR HUMAN HEIGHT MEASUREMENT

(75) Inventors: Peter Staats, Wenham, MA (US); Stephen Staats, Wenham, MA (US)

(73) Assignee: Zoe Medical Incorporated, Topsfield, MA (US)

( * ) Notice: Subject to any disclaimer, the term of this patent is extended or adjusted under 35 U.S.C. 154(b) by 249 days.

(21) Appl. No.: 13/199,464

(22) Filed: Aug. 31, 2011

(65) Prior Publication Data

US 2012/0065916 A1 Mar. 15, 2012

Related U.S. Application Data

(60) Provisional application No. 61/403,074, filed on Sep. 10, 2010.

(51) Int. Cl.
*G01C 25/00* (2006.01)
*A61B 5/107* (2006.01)
*A61B 5/00* (2006.01)

(52) U.S. Cl.
CPC ............. *A61B 5/1072* (2013.01); *A61B 5/1079* (2013.01); *A61B 2560/0223* (2013.01); *A61B 5/6814* (2013.01)

(58) Field of Classification Search
CPC ......... G06F 19/00; A61B 5/103; G01B 11/02
USPC ............................ 702/97, 135, 143, 159, 166
See application file for complete search history.

(56) References Cited

U.S. PATENT DOCUMENTS

| | | | |
|---|---|---|---|
| 4,336,855 A | 6/1982 | Chen | |
| 4,518,052 A | 5/1985 | Chen | |
| 4,923,024 A | 5/1990 | Ferrer | |
| 5,763,837 A * | 6/1998 | Davignon et al. | 174/113 R |
| 6,847,586 B1 * | 1/2005 | Chen | 367/99 |
| 7,006,405 B1 * | 2/2006 | Huang | 367/107 |
| 7,200,952 B2 | 4/2007 | Montagnino | |
| 7,327,442 B1 * | 2/2008 | Fear et al. | 356/4.08 |
| 8,109,008 B1 * | 2/2012 | Niemczak et al. | 33/832 |
| 8,279,410 B2 * | 10/2012 | Pan | 356/3.05 |
| 2002/0010393 A1 * | 1/2002 | Israel | 600/398 |
| 2005/0280533 A1 | 12/2005 | Yao | |
| 2006/0205524 A1 | 9/2006 | Foster | |
| 2010/0103405 A1 | 4/2010 | Pan | |
| 2010/0298708 A1 * | 11/2010 | Pan | 600/449 |
| 2010/0321149 A1 | 12/2010 | Foster | |

* cited by examiner

*Primary Examiner* — Janet Suglo

(57) ABSTRACT

A method for measuring the height of a person is provided. A person is positioned in a room having a floor and a ceiling, and the method comprises the steps of: i) providing a measuring device; ii) calibrating the measuring device to determine a first distance from the floor to the ceiling; iii) placing the measuring device on the person's head; iv) measuring a second distance from the person's head to the ceiling; and v) subtracting the second distance from the first distance to calculate the person's height. An apparatus for performing the measurement is also included.

9 Claims, 4 Drawing Sheets

METHOD AND APPARATUS FOR HUMAN HEIGHT MEASUREMENT

CROSS-REFERENCE TO RELATED APPLICATION

This application claims priority to Provisional Application Ser. No. 61/403,074, filed Sep. 10, 2010, incorporated by reference in its entirety.

BACKGROUND

1. Field of the Invention

This invention relates to a method of measuring a person's height and an associated apparatus for implementation of the method.

2. Description of Prior Art

Typical height measurement devices used in doctors' offices consist of a vertical member marked with a height scale and attached either to the wall or to a floor base. These devices measure a person's height relative to the floor, often using a movable horizontal member which slides up and down the vertical member and indicates the person's height as a position on the vertical height scale when the horizontal member is rested on the person's head. Electronic measurement approaches in these devices usually center on tracking the vertical position of the movable horizontal member electronically and displaying the associated height measurement. Such electronic measurement approaches are expensive and offer little advantage over reading the height measurement manually from a printed scale.

Other electronic distance measurement technologies, such as ultrasonic or laser range finding, are sufficiently accurate and cheaper. However, these sensors cannot be placed directly on top of a patient's head and measure the distance to the floor. In order to measure the distance to the floor, these sensors need a clear line of sight to the floor. Offsetting the sensors from the patient's head far enough to provide this line of sight adds mechanical complexity to measurement devices and increases the potential for error due to the sensors not being level with the top of the patient's head. Additionally, there is a possibility that a downward-looking sensor will detect some object closer than the floor and therefore give an inaccurate height measurement.

SUMMARY

Accordingly, in one aspect the invention provides a method for measuring the height of a person positioned in a room having a floor and a ceiling, the method comprising the steps of: i) providing a measuring device; ii) calibrating the measuring device to determine a first distance from the floor to the ceiling; iii) placing the measuring device on the person's head; iv) measuring a second distance from the person's head to the ceiling; and v) subtracting the second distance from the first distance to calculate the person's height.

In additional aspects, the invention provides an apparatus for measuring a person's height, the person positioned in a room having a floor and a ceiling, the apparatus comprising: i) a measuring component and associated software to measure a first distance from the floor to the ceiling and a second distance from the person's head to the ceiling; ii) software to calculate the person's height based on the first and second distances.

DESCRIPTION OF THE DRAWINGS

The invention is further illustrated by the following non-limiting drawings in which.

REFERENCE NUMERALS IN DRAWINGS

Figure 1:
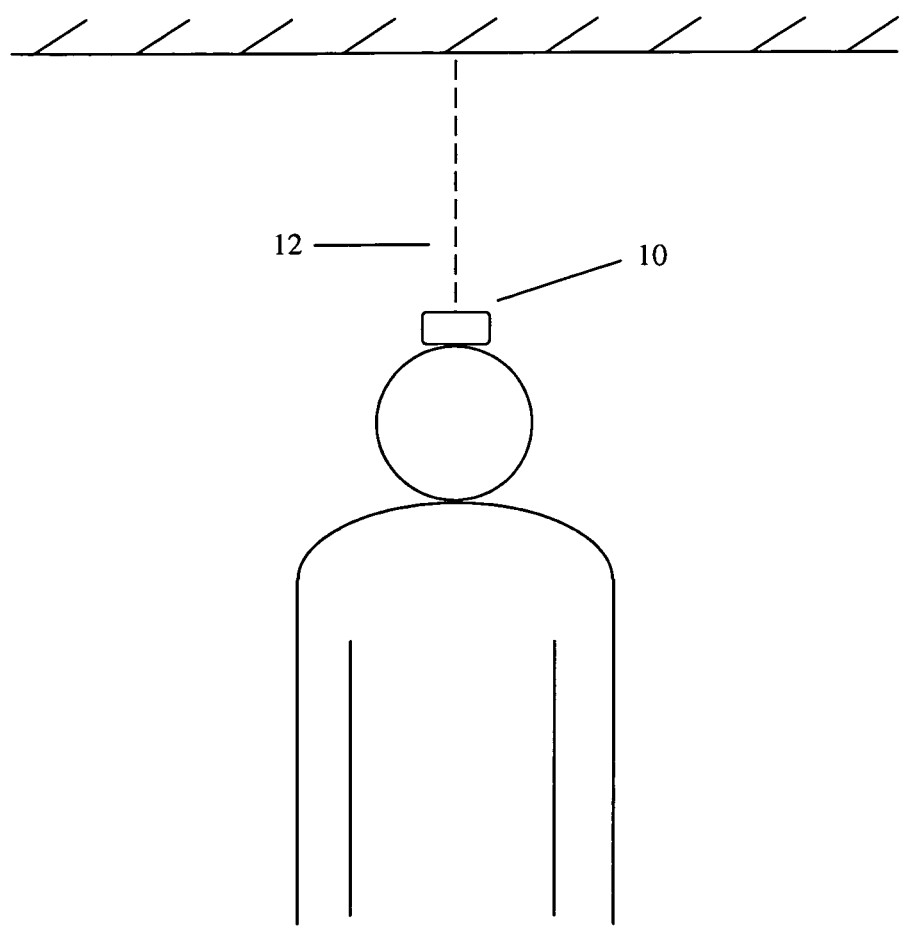
FIG. 1 shows the measurement of a person's height through determining the vertical distance between the person's head and the ceiling of a room.

10) Height measurement device
12) Vertical distance from person's head to ceiling of a room
14) Angle with respect to vertical of a distance measurement from a person's head to the ceiling of a room
16) Laser beam
18) Vertical distance from the floor to the ceiling of a room
20) Laser range finder
22) Inclinometer
24) Microcontroller
26) User Interface
28) Wired electronic interface to other equipment
30) Wireless electronic interface to other equipment

DETAILED DESCRIPTION OF THE INVENTION

In some embodiments, the invention provides a human height measuring method suitable for use with low-cost electronic height measuring devices. Suitable electronic measuring devices include, for example, lasers, infrared, and ultrasonic measuring devices. Some commercially available electronic measurement devices include Leica Disto laser rangefinders, IR range sensors made by Sharp Corporation, or Parallax's Ping))) ultrasonic range sensor.

In some embodiments, the invention provides a human height measuring method which allows for the use of portable measuring devices which do not need to be fixed to the wall of a room or occupy floor space. Use of an electronic height measurement device provides high accuracy height measurement data and improves ease of use.

Taking a measurement up from the patient's head to the ceiling instead of down to the floor results in accurate height measurements when the electronic sensor is placed directly on top of a patient's head. This eliminates the complexity and associated potential for error introduced by offsetting measurement sensors from the patient's head. An upward-facing sensor is also less prone to the downward-facing sensor problem of detecting an extraneous object rather than measuring to the floor. Since ceilings usually have far fewer objects on them than floors do, upward facing sensors have a greatly reduced probability of detecting an extraneous object rather than measuring to the ceiling.

Using a distance measurement sensor placed on top of the patient's head eliminates the need for a measurement device either attached any wall or ceiling, or mounted on a floor base, which saves wall and floor space as well as allowing height measurements to be taken anywhere in the room rather than in the one place where a fixed measurement device would be installed.

A distance measurement device that measures to the ceiling also improves ease of use, since a patient's height may be measured simply by placing the device on top of the patient's head. This eliminates the difficulty and associated inaccuracy of a significantly shorter person attempting to measure the height of a tall person by gauging the tall person's height against a vertically mounted height scale.

Figure 2:
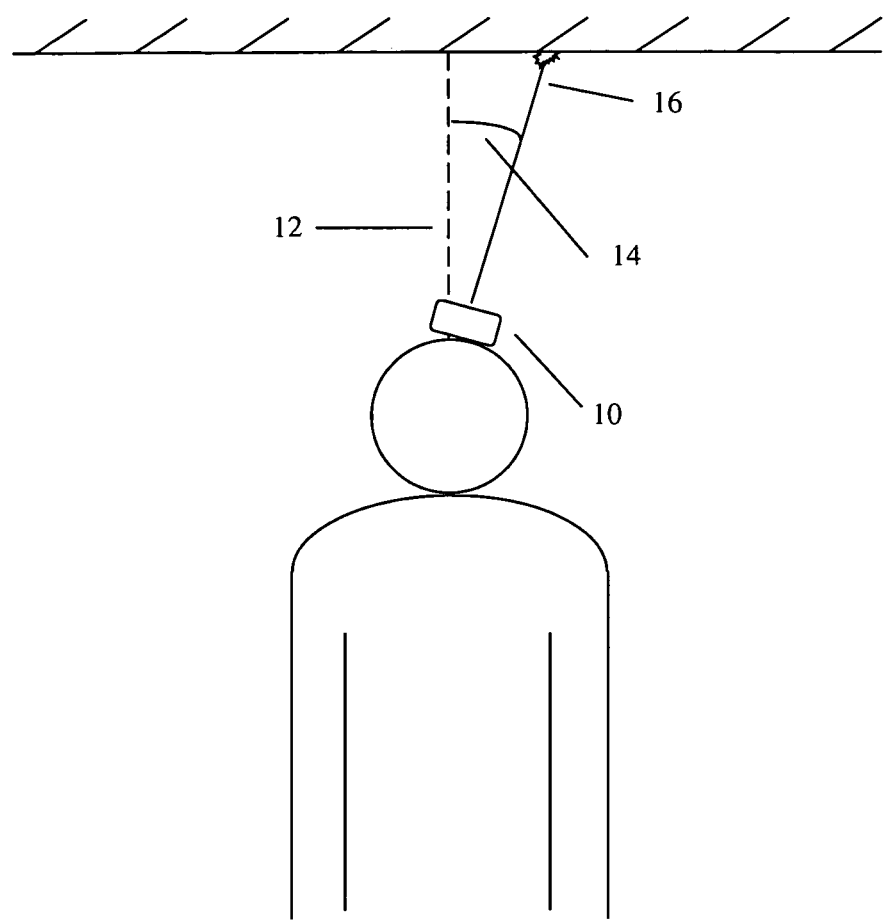
FIG. 2 shows the measurement of a person's height with an electronic device which includes a laser range finder for distance measurement. The measurement shown is not perfectly vertical.
Figure 3:
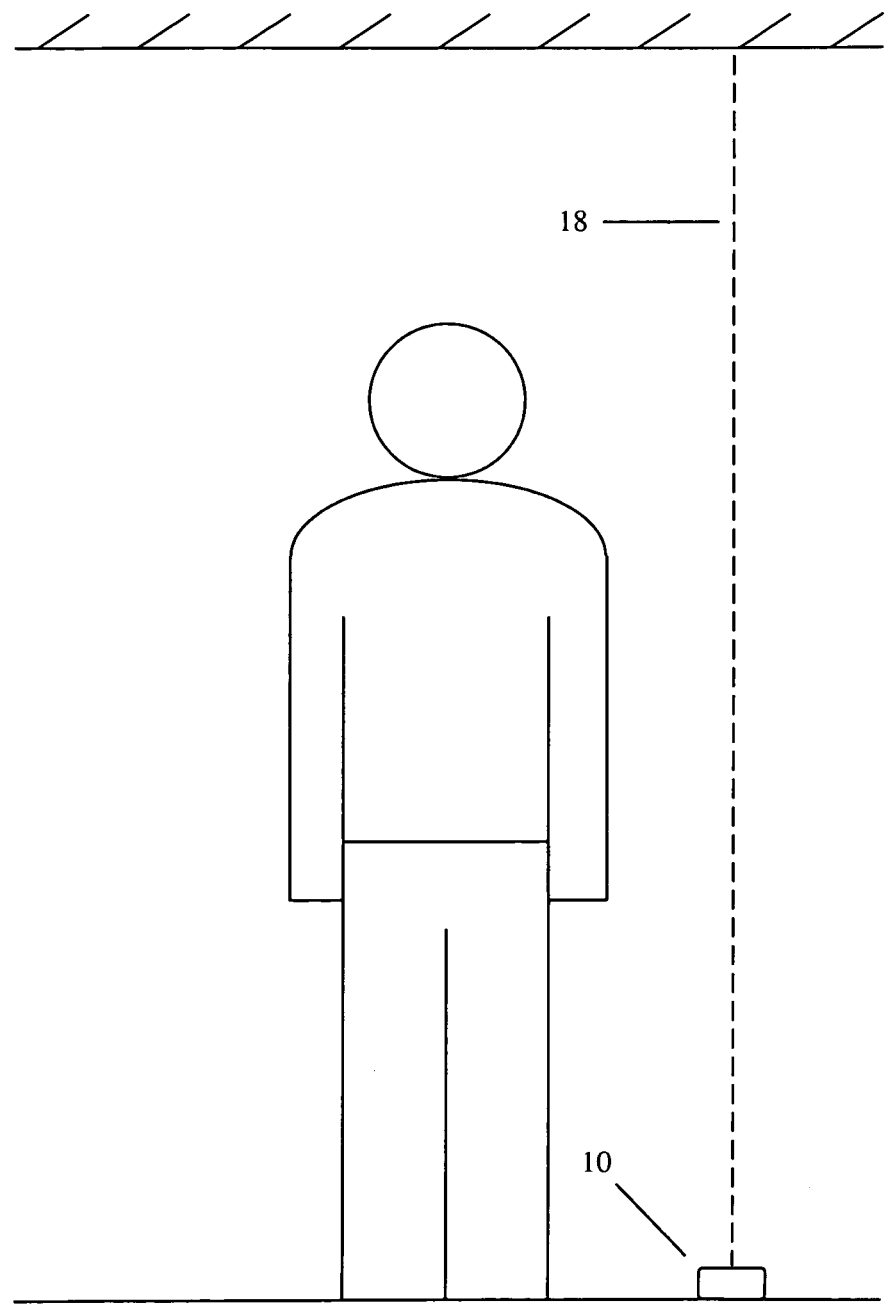
FIG. 3 shows the calibration of the height measurement device through its use to measure the ceiling height of a room.
Figure 4:
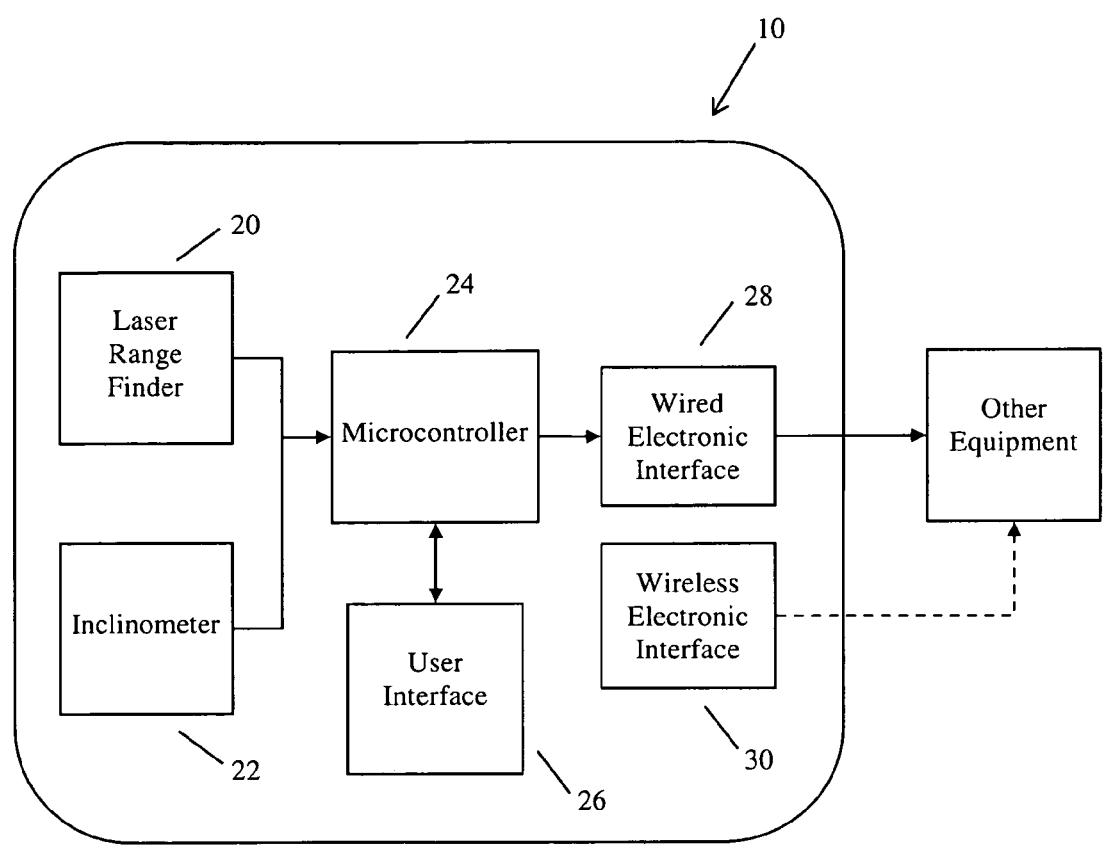
FIG. 4 is a block diagram of a preferred embodiment of the height measurement device including a laser range finder, an inclinometer, a microcontroller, a user interface, and wired and/or wireless electronic interfaces for communicating with other equipment.

Referring now to the figures, FIG. 1 shows the use of the height measurement device [10] in its simplest form. The device is placed on a person's head, and it measures the vertical distance [12] to the ceiling from the person's head. Given the height of the room, this measurement makes it possible to calculate the person's height. FIG. 2 shows an additional embodiment of the height measurement device. In this embodiment, the device measures the distance from a person's head to the ceiling using a laser beam [16]. Also, FIG. 2 shows the likely case in which the distance measurement to the ceiling is at an angle with respect to vertical [14]. FIG. 3 illustrates the use of the height measurement device to self-calibrate by measuring the vertical distance from the floor to the ceiling of a room [18]. FIG. 4 is a block diagram of a preferred embodiment of the height measurement device including a laser range finder [20], which enables the device to make electronic distance measurements. The preferred embodiment also includes an inclinometer [22] to quantify any deviation from vertical in a distance measurement from a person's head to the ceiling of a room. Knowing a distance measurement's angle with respect to vertical [14] makes it possible to calculate the true vertical distance to the ceiling. Finally, a preferred embodiment of the device includes a microcontroller [24] to perform height calculations, a user interface [26] for using the device, and an electronic interface, either wired [28] or wireless [30], to communicate measurement data to other equipment.

In operation, the invention measures the height of a human subject by determining the distance from the top of the person's head to the ceiling of the room where the person is standing. Subtracting the distance measured from the top of the person's head to the ceiling of the room from the height of the room yields the height of the person. If the angle of measurement is not perfectly vertical, and inclinometer is used to measure the deviation from vertical, and the height calculation is adjusted for the deviation.

In preferred embodiments an apparatus according to the invention is a small, handheld electronic device that measures the distance to the ceiling when placed on a person's head. The device then calculates the person's height based on the known height of the ceiling. Such a device might make use of a distance measurement technology such as laser range finding, incorporate a microcontroller to perform the measurements, and include a user interface that allows a user to operate the device and view measurements.

Calculating a person's height accurately depends on determining the vertical distance from the top of their head to the ceiling. If the measurement from the person's head to the ceiling is made at any angle with respect to the vertical, error will be introduced. In order to compensate for likely errors resulting from imperfectly vertical measurements, in a preferred embodiment an inclinometer is included to measure the actual angle with respect to vertical of the measurement vector from the person's head to the ceiling. Knowing the measured distance from the person's head to the ceiling and the angle with respect to vertical of the measurement vector permits the determination of the true vertical distance from the patient's head to the ceiling. One skilled in the art may calculate the true vertical distance by simple application of trigonometry. In some embodiments, the apparatus of the invention includes software for performing this calculation.

Since calculating a person's height depends on knowing the height of the ceiling in the room where a person's height is measured, in a preferred embodiment the invention incorporates the capability of measuring the height of a room, by placing the device on the floor and measuring the distance from the floor to the ceiling.

In additional embodiments, an apparatus according to the invention includes an electronic interface—wired or wireless—to communicate with other equipment—including, but not limited to, a medical patient monitor or a computer system in a hospital or physician's office.

Whereas particular embodiments of this invention have been described above for purposes of illustration, it will be evident to those skilled in the art that numerous variations of the details of the invention may be made without departing from the invention as defined in the appended claims.

We claim:

1. A method for measuring the height of a person positioned in a room having a floor and a ceiling, the method comprising the steps of:
    i) providing a portable handheld electronic measuring device;
    ii) calibrating said measuring device by placing said measuring device on said floor to measure a first distance from said floor to said ceiling;
    iii) correcting for imperfectly vertical measurement of said first distance that may result from said measuring device not being placed parallel to said ceiling in order to compute a corrected first distance;
    iv) placing said measuring device in contact with the top of said person's head;
    v) measuring a second distance from the top of said person's head to said ceiling;
    vi) correcting for imperfectly vertical measurement of said second distance that may result from said measuring device not being held parallel to said ceiling in order to compute a corrected second distance; and
    vii) subtracting said corrected second distance from said corrected first distance to calculate said person's height.

2. The method of claim 1, wherein the measuring device uses a laser range finder to measure distances.

3. The method of claim 1, wherein the measuring device uses an ultrasonic range finder to measure distances.

4. The method of claim 1, wherein an inclinometer is used to quantify deviation from vertical of said imperfectly vertical measurement.

5. An apparatus for measuring a person's height, the person positioned in a room having a floor and a ceiling, the apparatus comprising:
    i) a portable handheld electronic measuring device;
    ii) a means for signaling said measuring device to take a calibration measurement;
    iii) a means to calibrate said measuring device by placing said measuring device on said floor to measure a first distance from said floor to said ceiling;
    iv) an inclinometer to correct for imperfectly vertical measurement of said first distance that may result from said measuring device not being held parallel to said ceiling in order to compute a corrected first distance;
    v) a means for signaling said measuring device to take a height measurement when said measuring device is in contact with the top of said person's head;
    vi) a means to measure a second distance from the top of said person's head to said ceiling;

vii) a means using said inclinometer to correct for imperfectly vertical measurement of said second distance that may result from said measuring device not being held parallel to said ceiling in order to compute a corrected second distance;
viii) software to subtract said corrected second distance from said corrected first distance to compute a height measurement; and
ix) a means for recording the result of said height measurement.

6. The apparatus of claim 5, wherein the signaling means comprises a button on the device and the recording means comprises a display on the device.

7. The apparatus of claim 5, wherein the means to measure height comprises a laser range finder.

8. The apparatus of claim 5, wherein the means to measure height comprises an ultrasonic range finder.

9. The apparatus of claim 5, further comprising a wired or wireless electronic interface for communicating with one or more secondary devices.

* * * * *